(12) United States Patent
Dassler et al.

(10) Patent No.: US 12,084,664 B2
(45) Date of Patent: Sep. 10, 2024

(54) BACTERIAL LPP MUTANTS AND THE USE THEREOF FOR THE SECRETORY PRODUCTION OF RECOMBINANT PROTEINS

(71) Applicant: WACKER CHEMIE AG, Munich (DE)

(72) Inventors: Tobias Dassler, Munich (DE); Marian Kujau, Jena (DE)

(73) Assignee: WACKER CHEMIE AG, Munich (DE)

( * ) Notice: Subject to any disclaimer, the term of this patent is extended or adjusted under 35 U.S.C. 154(b) by 849 days.

(21) Appl. No.: 17/262,057

(22) PCT Filed: Jul. 24, 2018

(86) PCT No.: PCT/EP2018/069984
§ 371 (c)(1),
(2) Date: Jan. 21, 2021

(87) PCT Pub. No.: WO2020/020438
PCT Pub. Date: Jan. 30, 2020

(65) Prior Publication Data
US 2021/0301297 A1    Sep. 30, 2021

(51) Int. Cl.
| | |
|---|---|
| C12N 15/70 | (2006.01) |
| C12N 1/20 | (2006.01) |
| C12N 15/67 | (2006.01) |
| C12R 1/19 | (2006.01) |

(52) U.S. Cl.
CPC ............ *C12N 15/70* (2013.01); *C12N 1/20* (2013.01); *C12N 15/67* (2013.01); *C12R 2001/19* (2021.05)

(58) Field of Classification Search
CPC .......... C12N 15/70; C12N 1/20; C12N 15/67; C12R 2001/19
See application file for complete search history.

(56) References Cited

U.S. PATENT DOCUMENTS

| | | |
|---|---|---|
| 5,223,482 A | 6/1993 | Schilling, Jr. et al. |
| 6,514,730 B1 | 2/2003 | Schmid et al. |
| 8,053,211 B2 | 11/2011 | Dassler et al. |
| 2008/0076157 A1 | 3/2008 | Leonhartsberger et al. |
| 2008/0076158 A1* | 3/2008 | Dassler .......... C12Y 204/01019 435/71.2 |
| 2008/0254511 A1 | 10/2008 | Dassler et al. |

FOREIGN PATENT DOCUMENTS

| | | |
|---|---|---|
| CN | 102827860 B | 6/2014 |
| EP | 0448093 B1 | 3/1996 |
| EP | 2204441 B1 | 7/2011 |
| EP | 1905839 B2 | 7/2019 |

OTHER PUBLICATIONS

Chang, Ting-Wei, et al. "Outer membrane lipoprotein Lpp is Gram-negative bacterial cell surface receptor for cationic antimicrobial peptides." Journal of Biological Chemistry 287.1 (2012): 418-428 (Year: 2012).*
Earhart, Charles F. "[30] Use of an Lpp-OmpA fusion vehicle for bacterial surface display." Methods in enzymology. vol. 326. Academic Press, 2000. 506-516 (Year: 2000).*
Yakushi, Toshiharu, et al. "Lethality of the covalent linkage between mislocalized major outer membrane lipoprotein and the peptidoglycan of *Escherichia coli*." Journal of bacteriology 179.9 (1997): 2857-2862. (Year: 1997).*
Wolfram Zueckert et al., "Secretion of Bacterial Lipoproteins: Through the Cytoplasmic Membrane, the Periplasm and Beyond", Biochimica Et Biophysica Acta Molecular Cell Research 1843, 2014, vol. 8, pp. 1509-1516, Elsevier, NL.
Chou Z. Giam et al., "Characterization of a Novel Lipoprotein Mutant in *Escherichia coli*", The Journal of Biological Chemistry, May 10, 1984, vol. 259, No. 9, pp. 5601-5605, US.
Ting-Wei Chang et al., "Outer Membrane Lipoprotein Lpp Is Gram-negative Bacterial Cell Surface Receptor for Cationic Antimicrobial Peptides", Journal of Biological Chemistry, 2012, vol. 287, No. 1, pp. 418-428, American Society for Biochemistry and Molecular Biology, US.
Jian Sha et al., "Braun Lipoprotein (Lpp) Contributes to Virulence of Yersiniae: Potential Role of Lpp in Inducing Bubonic and Pneumonic Plague", Infection and Immunity, 2008, vol. 76, No. 4, pp. 1390-1409, American Society for Microbiology, US.
Kirill A. Datsenko et al., "One-step inactivation of chromosomal genes in *Escherichia coli* K-12 using PCR products", Proc. Natl. Acad. Sci. (PNSA) U.S.A., Jun. 6, 2000, vol. 97, No. 12, pp. 6640-6645.

(Continued)

*Primary Examiner* — Neil P Hammell
*Assistant Examiner* — John Charles McKillop
(74) *Attorney, Agent, or Firm* — BROOKS KUSHMAN P.C.

(57) ABSTRACT

An *Escherichia coli* bacterial strain contains a gene encoding a recombinant protein and an open reading frame of
  i) a DNA fragment encoding an N-terminal signal peptide which mediates translocation of the protein into the periplasm,
    wherein the N-terminal signal peptide is an amino acid sequence with at least 80% correspondence in relation to SEQ ID No. 2 from amino acids 1 to 20 or is a signal peptide of lipoproteins Pal, NlpI, NlpB or OsmB of *Escherichia coli*,
  linked to
  ii) a following DNA sequence (lpp(N)) encoding a lipoprotein (Lpp(N)) which, compared to SEQ ID No. 2 from amino acids 21 to 78, is a different in at most ten amino acids and
  iii) a further DNA sequence (lpp(C)) encoding a lipoprotein (Lpp(C)) which, compared to SEQ ID No. 2 from amino acids 21 to 78, is a different in at most ten amino acids.

11 Claims, 2 Drawing Sheets
Specification includes a Sequence Listing.

(56) References Cited

OTHER PUBLICATIONS

Chou-Zen Giam et al., "Prolipoprotein modification and processing in *Escherichia coli*", European Journal of Biochemistry, 1984, vol. 141, pp. 331-337, Wiley, UK.

Shigeru Hayashi et al., "Lipoproteins in Bacteria", Journal of Bioenergetics and Biomembranes, 1990, vol. 22, No. 3, Springer, Germany.

Y. Hirota et al., "On the process of cellular division in *Escherichia coli*: A mutant of *E. coli* lacking a murein-lipoprotein", Proc. Natl. Acad. Sci. (PNSA) USA, Apr. 1977, vol. 74, No. 4, pp. 1417-1420.

Robert M. Horton et al., "Gene Splicing by Overlap Extension: Tailor-Made Genes Using the Polymerase Chain Reaction", BioTechniques, 2013, vol. 54, No. 3, pp. 129-133.

Sumiko Inouye et al., "Amino Acid Replacement in a Mutant Lipoprotein of the *Escherichia coli* Outer Membrane", Journal of Bacteriology, Oct. 1977, vol. 132, No. 1, pp. 308-313, American Society for Microbiology, U.S.A.

Martin Kangwa et al., "High-level fed-batch fermentative expression of an engineered Staphylococcal protein A based ligand in *E. coli*: purification and characterization", AMB Express, 2015, vol. 5, No. 70, pp. 1-10, Springer Verlag, Germany.

Michael Karpusas et al., "Structure of CD40 Ligand in Complex with the Fab Fragment of a Neutralizing Humanized Antibody", Structure, Apr. 2001, vol. 9, pp. 321-329, Elsevier Science Ltd.

Andrew J. Link et al., "Methods for Generating Precise Deletions and Insertions in the Genome of Wild-Type *Escherichia coli*: Application to Open Reading Frame Characterization", Journal of Bacteriology, Oct. 1997, vol. 179, No. 20, pp. 6228-6237, American Society for Microbiology.

Wei Sun et al., "Highly Efficient Method for Introducing Successive Multiple Scarless Gene Deletions and Markerless Gene Insertions into the Yersinia pestis Chromosome", Applied and Environmental Microbiology, Jul. 2008, vol. 74, No. 13, pp. 4241-4245, American Society for Microbiology.

Hideho Suzuki et al., "Murein-Lipoprotein of *Escherichia coli*: A Protein Involved in the Stabilization of Bacterial Cell Envelope", Molec. Gen. Genet. (MGG), 1979, vol. 167, pp. 1-9, Springer Verlag, Germany.

\* cited by examiner

Fig. 1: Schematic representation of the unprocessed Lpp fusion protein (A), the unprocessed Lpp wild-type protein (B), and the unprocessed Lpp fusion protein 2xLppΔ (C) used in the examples.
A)
B)
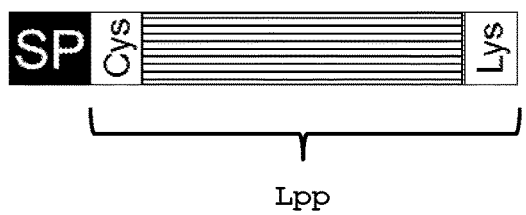
C)
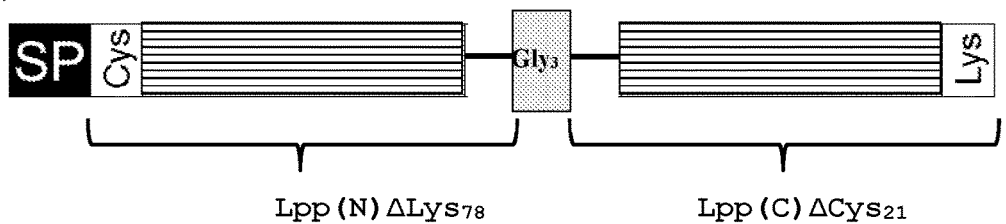

400

SEQUENCE LISTING

<160> NUMBER OF SEQ ID NOS: 17

<210> SEQ ID NO 1
<211> LENGTH: 237
<212> TYPE: DNA
<213> ORGANISM: Escherichia coli
<220> FEATURE:
<221> NAME/KEY: gene
<222> LOCATION: (1)..(237)
<223> OTHER INFORMATION: coding sequence of the lpp wild-type gene

<400> SEQUENCE: 1
atgaaagcta ctaaactggt actgggcgcg gtaatcctgg ttctactct gctggcaggt        60 tgctccagca acgctaaaat cgatcagctg tcttctgacg ttcagactct gaacgctaaa       120
gttgaccagc tgagcaacga cgtgaacgca atgcgttccg acgttcaggc tgctaaagat      180
gacgcagctc gtgctaacca gcgtctggac aacatggcta ctaaataccg caagtaa         237

<210> SEQ ID NO 2

```
<211> LENGTH: 78
<212> TYPE: PRT
<213> ORGANISM: Escherichia coli
<220> FEATURE:
<221> NAME/KEY: PROPEP
<222> LOCATION: (1)..(78)
<223> OTHER INFORMATION: unprocessed Lpp wild-type protein

<400> SEQUENCE: 2

Met Lys Ala Thr Lys Leu Val Leu Gly Ala Val Ile Leu Gly Ser Thr
1               5                   10                  15

Leu Leu Ala Gly Cys Ser Ser Asn Ala Lys Ile Asp Gln Leu Ser Ser
            20                  25                  30

Asp Val Gln Thr Leu Asn Ala Lys Val Asp Gln Leu Ser Asn Asp Val
        35                  40                  45

Asn Ala Met Arg Ser Asp Val Gln Ala Ala Lys Asp Asp Ala Ala Arg
    50                  55                  60

Ala Asn Gln Arg Leu Asp Asn Met Ala Thr Lys Tyr Arg Lys
65                  70                  75

<210> SEQ ID NO 3
<211> LENGTH: 137
<212> TYPE: PRT
<213> ORGANISM: Escherichia coli
<220> FEATURE:
<221> NAME/KEY: PROPEP
<222> LOCATION: (1)..(137)
<223> OTHER INFORMATION: unprocessed 2xLpp? protein

<400> SEQUENCE: 3

Met Lys Ala Thr Lys Leu Val Leu Gly Ala Val Ile Leu Gly Ser Thr
1               5                   10                  15

Leu Leu Ala Gly Cys Ser Ser Asn Ala Lys Ile Asp Gln Leu Ser Ser
            20                  25                  30

Asp Val Gln Thr Leu Asn Ala Lys Val Asp Gln Leu Ser Asn Asp Val
        35                  40                  45

Asn Ala Met Arg Ser Asp Val Gln Ala Ala Lys Asp Asp Ala Ala Arg
    50                  55                  60

Ala Asn Gln Arg Leu Asp Asn Met Ala Thr Lys Tyr Arg Gly Gly
65                  70                  75                  80

Ser Ser Asn Ala Lys Ile Asp Gln Leu Ser Ser Asp Val Gln Thr Leu
            85                  90                  95

Asn Ala Lys Val Asp Gln Leu Ser Asn Asp Val Asn Ala Met Arg Ser
            100                 105                 110

Asp Val Gln Ala Ala Lys Asp Asp Ala Ala Arg Ala Asn Gln Arg Leu
            115                 120                 125

Asp Asn Met Ala Thr Lys Tyr Arg Lys
    130                 135

<210> SEQ ID NO 4
<211> LENGTH: 90
<212> TYPE: DNA
<213> ORGANISM: Klebsiella pneumoniae M5a1
<220> FEATURE:
<221> NAME/KEY: sig_peptide
<222> LOCATION: (1)..(90)
<223> OTHER INFORMATION: signal peptide

<400> SEQUENCE: 4
atgaaaagaa accgtttttt taatacctcg gctgctattg ccatttcgat tgcattaaat      60
actttttttt gtagcatgca gacgattgct                                       90
```

<210> SEQ ID NO 5
<211> LENGTH: 90
<212> TYPE: DNA
<213> ORGANISM: artificial
<220> FEATURE:
<221> NAME/KEY: sig_peptide
<222> LOCATION: (1)..(90)
<223> OTHER INFORMATION: artificial signal peptide

<400> SEQUENCE: 5
atgaaaagaa accgtttttt taatacctcg gctgctattg ccatttcgat tgcattacag    60
atcttttttc cgtccgcttc cgctttcgct                                     90

<210> SEQ ID NO 6
<211> LENGTH: 78
<212> TYPE: DNA
<213> ORGANISM: artificial
<220> FEATURE:
<221> NAME/KEY: misc_feature
<222> LOCATION: (1)..(78)
<223> OTHER INFORMATION: oligonucleotide lpp-cat-sac-fw

<400> SEQUENCE: 6
aactttgtgt aatacttgta acgctacatg gagattaact caatctagag ggtattaata    60
gccctgggcc aactttg                                                   78

<210> SEQ ID NO 7
<211> LENGTH: 78
<212> TYPE: DNA
<213> ORGANISM: artificial
<220> FEATURE:
<221> NAME/KEY: misc_feature
<222> LOCATION: (1)..(78)
<223> OTHER INFORMATION: oligonucleotide lpp-cat-sac-rev

<400> SEQUENCE: 7
taaacggcag acaaaaaaaa tggcgcacaa tgtgcgccat ttttcacttc acaggtacta    60
acactgcttc cggtagtc                                                  78

<210> SEQ ID NO 8
<211> LENGTH: 23
<212> TYPE: DNA
<213> ORGANISM: artificial
<220> FEATURE:
<221> NAME/KEY: misc_feature
<222> LOCATION: (1)..(23)
<223> OTHER INFORMATION: oligonucleotide pykF

<400> SEQUENCE: 8
ctcgcgcagt acgtaaatac ttc                                            23

<210> SEQ ID NO 9
<211> LENGTH: 21
<212> TYPE: DNA
<213> ORGANISM: artificial
<220> FEATURE:
<221> NAME/KEY: misc_feature
<222> LOCATION: (1)..(21)
<223> OTHER INFORMATION: oligonucleotide ynhG2

<400> SEQUENCE: 9
cgtctttgct tacactcacg c                                              21

<210> SEQ ID NO 10

```
<211> LENGTH: 22
<212> TYPE: DNA
<213> ORGANISM: artificial
<220> FEATURE:
<221> NAME/KEY: misc_feature
<222> LOCATION: (1)..(22)
<223> OTHER INFORMATION: oligonucleotide lpp-Allel-fw

<400> SEQUENCE: 10
atttgtatat cgaagcgccc tg                                           22

<210> SEQ ID NO 11
<211> LENGTH: 80
<212> TYPE: DNA
<213> ORGANISM: artificial
<220> FEATURE:
<221> NAME/KEY: misc_feature
<222> LOCATION: (1)..(80)
<223> OTHER INFORMATION: oligonucleotide lpp-2x-rev2

<400> SEQUENCE: 11
cattcagggt ctgcacatcg ctgctcagtt gatcaatttt ggcgttagag cttccgccac   60
cgcggtattt agtagccatg                                              80

<210> SEQ ID NO 12
<211> LENGTH: 60
<212> TYPE: DNA
<213> ORGANISM: artificial
<220> FEATURE:
<221> NAME/KEY: misc_feature
<222> LOCATION: (1)..(60)
<223> OTHER INFORMATION: oligonucleotide lpp-2x-rev3

<400> SEQUENCE: 12
acgcattgca ttaacatcgt ttgacagctg atccactttc gcattcaggg tctgcacatc   60

<210> SEQ ID NO 13
<211> LENGTH: 62
<212> TYPE: DNA
<213> ORGANISM: artificial
<220> FEATURE:
<221> NAME/KEY: misc_feature
<222> LOCATION: (1)..(62)
<223> OTHER INFORMATION: oligonucleotide lpp-2x-fw2

<400> SEQUENCE: 13
gcgcaaatca gcgcctggat aatatggcaa ccaagtatcg taaataatag tacctgtgaa   60
gt                                                                 62

<210> SEQ ID NO 14
<211> LENGTH: 21
<212> TYPE: DNA
<213> ORGANISM: artificial
<220> FEATURE:
<221> NAME/KEY: misc_feature
<222> LOCATION: (1)..(21)
<223> OTHER INFORMATION: oligonucleotide lpp-Allel-rev

<400> SEQUENCE: 14
cagaagaaca gcagaacgtt c                                            21

<210> SEQ ID NO 15
<211> LENGTH: 75
<212> TYPE: DNA
<213> ORGANISM: artificial
<220> FEATURE:
<221> NAME/KEY: misc_feature
```

```
<222> LOCATION: (1)..(75)
<223> OTHER INFORMATION: oligonucleotide lpp-2x-fw3

<400> SEQUENCE: 15
caaacgatgt taatgcaatg cgtagcgatg tgcaggcagc aaaggatgat gcagcacgcg    60
caaatcagcg cctgg                                                     75

<210> SEQ ID NO 16
<211> LENGTH: 1005
<212> TYPE: DNA
<213> ORGANISM: artificial
<220> FEATURE:
<221> NAME/KEY: misc_feature
<222> LOCATION: (293)..(706)
<223> OTHER INFORMATION: expression cassette 2xlpp?

<400> SEQUENCE: 16
atttgtatat cgaagcgccc tgatgggcgc ttttttatt taatcgataa ccagaagcaa    60
taaaaaatca atcggattt cactatataa tctcactta tctaagatga atccgatgga    120
agcatcctgt tttctctcaa ttttttatc taaaacccag cgttcgatgc ttctttgagc   180
gaacgatcaa aaataagtgc cttcccatca aaaaaatatt ctcaacataa aaactttgt   240 gtaatacttg taacgctaca tggagattaa ctcaatctag agggtattaa taatgaaagc   300
tactaaactg gtactgggcg cggtaatcct gggttctact ctgctggcag gttgctccag   360
caacgctaaa atcgatcagc tgtcttctga cgttcagact ctgaacgcta agttgacca   420 gctgagcaac gacgtgaacg caatgcgttc cgacgttcag gctgctaaag atgacgcagc   480
tcgtgctaac cagcgtctgg acaacatggc tactaaatac cgcggtggcg aagctctaa   540 cgccaaaatt gatcaactga gcagcgatgt gcagaccctg aatgcgaaag tggatcagct   600
gtcaaacgat gttaatgcaa tgcgtagcga tgtgcaggca gcaaaggatg atgcagcacg   660
cgcaaatcag cgcctggata atatggcaac caagtatcgt aaataatagt acctgtgaag   720
tgaaaaatgg cgcacattgt gcgccatttt ttttgtctgc cgtttaccgc tactgcgtca   780
cgcgtaacat attcccttgc tctggttcac cattctgcgc tgactctact gaaggcgcat   840
tgctggctgc gggagttgct ccactgctca ccgaaaccgg atacctgcc cgacgataca   900 acgctttatc gactaacttc tgatctacag ccttattgtc tttaaattgc gtaaagcctg   960
ctggcagtgt gtatggcatt gtctgaacgt tctgctgttc ttctg                  1005

<210> SEQ ID NO 17
<211> LENGTH: 1599
<212> TYPE: DNA
<213> ORGANISM: artificial
<220> FEATURE:
<221> NAME/KEY: misc_feature
<222> LOCATION: (25)..(1549)
<223> OTHER INFORMATION: anti-CD154 expression cassette
<220> FEATURE:
<221> NAME/KEY: sig_peptide
<222> LOCATION: (25)..(114)
<223> OTHER INFORMATION: AFA signal sequence
<220> FEATURE:
<221> NAME/KEY: misc_feature
<222> LOCATION: (115)..(777)
<223> OTHER INFORMATION: reading frame for HC (VH-CH1)
<220> FEATURE:
<221> NAME/KEY: sig_peptide
<222> LOCATION: (800)..(862)
<223> OTHER INFORMATION: phoA signal sequence
<220> FEATURE:
<221> NAME/KEY: misc_feature
<222> LOCATION: (863)..(1516)
```

<223> OTHER INFORMATION: reading frame for LC (VL-CL)
<220> FEATURE:
<221> NAME/KEY: misc_feature
<222> LOCATION: (1517)..(1546)
<223> OTHER INFORMATION: linker including His tag

<400> SEQUENCE: 17

```
acagaattct aaggaggaaa ttatatgaaa agaaaccgtt tttttaatac ctcggctgct      60
attgccattt cgattgcatt acagatcttt tttccgtccg cttccgcttt cgctcaggtt     120
cagctggtgc agagcggtgc cgaagttgtt aaaccgggtg caagcgttaa actgagctgt     180
aaagcaagcg gctatatttt taccagctat tatatgtatt gggtgaaaca ggcaccgggt     240
cagggtctgg aatggattgg tgaaattaat ccgagcaatg gcgataccaa tttaatgaa      300
aaatttaaaa gcaaagccac cctgaccgtt gataaaagcg caagcaccgc atatatggaa     360
ctgagcagcc tgcgtagcga agataccgca gtttattatt gtacccgtag tgatggtcgc     420
aatgatatgg atagctgggg tcagggcacc ctggtcaccg ttagcagcgc aagcaccaaa     480
ggtccgagcg ttttccgct ggcaccgagc agcaaaagca ccagcggtgg caccgcagca     540
ctgggttgtc tggttaaaga ttatttccg gaaccggtta cagttagctg gaatagcggt      600
gcactgacca gtggtgttca tacctttccg gcagttctgc aaagcagcgg tctgtatagc     660
ctgagcagcg ttgttaccgt tccgagcagt agcctgggca cccagaccta tatttgtaat     720
gttaatcata aaccgagcaa caccaaagtg gataaaaaag ttgaaccgaa aagctgctaa     780
taaccatgga gaaaataaag tgaaacaaag cactattgca ctggcactct accgttact      840
cttcacccct gttaccaaag ccgatattgt gctcacccag agtccggcaa ccctgagcgt     900
tagtccgggt gaacgtgcaa ccattagctg tcgtgcaagc cagcgtgtta gcagcagcac     960
ctatagctat atgcattggt atcagcagaa accgggtcag cctccgaaac tgctgattaa     1020
atatgcaagc aatctggaaa gcggtgttcc ggcacgtttt agcggtagcg gtagtggcac     1080
cgattttacc ctgaccatta gcagcgttga accggaagat tttgccacct attattgtca     1140
gcatagctgg gaaattcctc cgacctttgg tggtggcacc aaactcgaga ttaaacgtac     1200
cgttgcagca ccgagcgtgt ttatctttcc gccagtgat gaacagctga aaagcggcac     1260
cgcaagcgtt gtttgtctgc tgaataactt ttatccgcgt gaagcaaaag ttcagtggaa     1320
agttgataat gcactgcaaa gcggtaatag ccaagaaagc gttaccgaac aggatagcaa     1380
agatagcacc tatagcctgt caagcaccct gaccctgagc aaagcagatt atgaaaaaca     1440
caaagtgtat gcctgcgaag ttacccatca gggtctgagc agtccggtta caaaaagttt     1500
taatcgtggt gaatgtagct cttctgccca tcaccaccat caccattaat aagcttctag     1560
aagcttggct gttttggcgg atgagagaag attttcgac                            1599
```

BACTERIAL LPP MUTANTS AND THE USE THEREOF FOR THE SECRETORY PRODUCTION OF RECOMBINANT PROTEINS

CROSS REFERENCE TO RELATED APPLICATIONS

This application is the U.S. National Phase of PCT Appln. No. PCT/EP2018/069984 filed Jul. 24, 2018, the disclosure of which is incorporated in its entirety by reference herein.

SEQUENCE LISTING

The text file Sequence listing CO11805 of size 10 KB created Jan. 21, 2021, filed herewith, is hereby incorporated by reference.

BACKGROUND OF THE INVENTION

1. Field of the Invention

The invention relates to a novel bacterial lpp mutant and use thereof in a fermentation method for secretory production of recombinant proteins.

2. Description of the Related Art

The market for recombinant protein pharmaceuticals (pharmaproteins/biologics) has grown strongly in recent years. Particularly important protein pharmaceuticals are eukaryotic proteins, especially mammalian proteins and human proteins. Examples of important pharmaproteins (pharmaceutically active proteins) are cytokines, growth factors, protein kinases, protein and peptide hormones, and antibodies and antibody fragments. Because the production costs for pharmaproteins are still very high, there is an ongoing search for more efficient and hence more cost-effective methods and systems for the production thereof.

In general, recombinant proteins are produced either in mammalian cell cultures or in microbial systems. Compared to mammalian cell cultures, microbial systems have the advantage that it is possible in this way to produce recombinant proteins in a shorter time and at lower costs. Bacteria are therefore especially suitable for the production of recombinant proteins. Owing to its extensively studied genetics and physiology, the short generation time and the simple handling, the Gram-negative enterobacterium *Escherichia coli* (*E. coli*) is currently the most commonly used organism for production of recombinant proteins. What are particularly attractive are production methods in which the target protein is released directly into the fermentation medium in correct folding by the bacterial cells, since this dispenses with a complicated cell disruption and potentially an unprofitable protein refolding process. A further advantage of extracellular production is that the release of the target protein into the culture medium can often increase the product yield, since the accumulation of the target protein is not restricted to the space of the periplasm or of the cytoplasm.

Suitable for the extracellular production of a target protein are, for example, so-called "leaky" strains of *E. coli*, which discharge proteins situated in the periplasm into the medium to an increased extent owing to the absence of or the change in certain structural elements of the cell envelope. Such "leaky" strains may have altered proportions of lipoprotein in the outer membrane, as is the case, inter alia, in certain mutants in Braun's lipoprotein (lpp) (Inouye et al. 1977, J. Bact. 132, pages 308-313; Suzuki 1978, Mol. Gen. Genet. 167, pages 1-9; Giam et al. 1984, Eur. J. Biochem. 141, pages 331-379).

Industrial-scale production methods for heterologous proteins have been disclosed, in which different lpp mutants of *E. coli* are used to achieve a release of target proteins into the fermentation medium (US 2008/0254511 A1, U.S. Pat. No. 5,223,482 A).

However, owing to the higher tendency toward cell lysis, "leaky" strains have, in the production of some heterologous target proteins, the disadvantage that they lyse relatively early and strongly despite certain measures to stabilize the cells, such as, for example, the addition of increased amounts of Ca und Mg ions to the culture medium (see US 2008/0254511 A1), the result being that, firstly, the protein production phase is shortened and thus the product yield is lower than it could be in the case of a longer production phase, and secondly, the cell lysis leads to a rise in the viscosity of the medium, this being attributable especially to the DNA released upon cell lysis. As a result, the subsequent purification and recovery of the target protein is made more difficult, and this in turn leads to unnecessarily high process costs.

It is an object of the invention to provide a mutated bacterial strain for use in a fermentative method for producing a recombinant target protein, wherein the predominant portion of the target protein is secreted into the fermentation medium during culturing and the amount of target protein present in the culture medium is higher than in the case of bacterial strains disclosed in the prior art, i.e., the target protein is to be present in the culture medium in an increased yield.

SUMMARY OF THE INVENTION

These and other objects are achieved by a bacterial strain containing at least one gene encoding a recombinant protein, characterized in that
said bacterial strain contains an open reading frame consisting of
i a DNA fragment encoding an N-terminal signal peptide which mediates the translocation of the protein into the periplasm, linked to
ii a following DNA sequence (lpp(N)) encoding a lipoprotein (Lpp(N)) which, in comparison with the lipoprotein Lpp encoded by the wild-type lpp gene, has a difference in at most ten amino acids and
iii a further DNA sequence (lpp(C)) encoding a lipoprotein (Lpp(C)) which, in comparison with the lipoprotein (Lpp) encoded by the wild-type lpp gene, has a difference in at most ten amino acids.

BRIEF DESCRIPTION OF THE DRAWINGS

FIG. 1 shows a schematic representation of the unprocessed Lpp fusion protein (A, 2xLpp) in comparison with the unprocessed Lpp wild-type protein (B, Lpp, sequence specified in SEQ ID No. 2) and of the unprocessed Lpp fusion protein used in the examples (C, 2xLppΔ, sequence specified in SEQ ID No. 3).

DETAILED DESCRIPTION OF THE PREFERRED EMBODIMENTS

Figure 2:
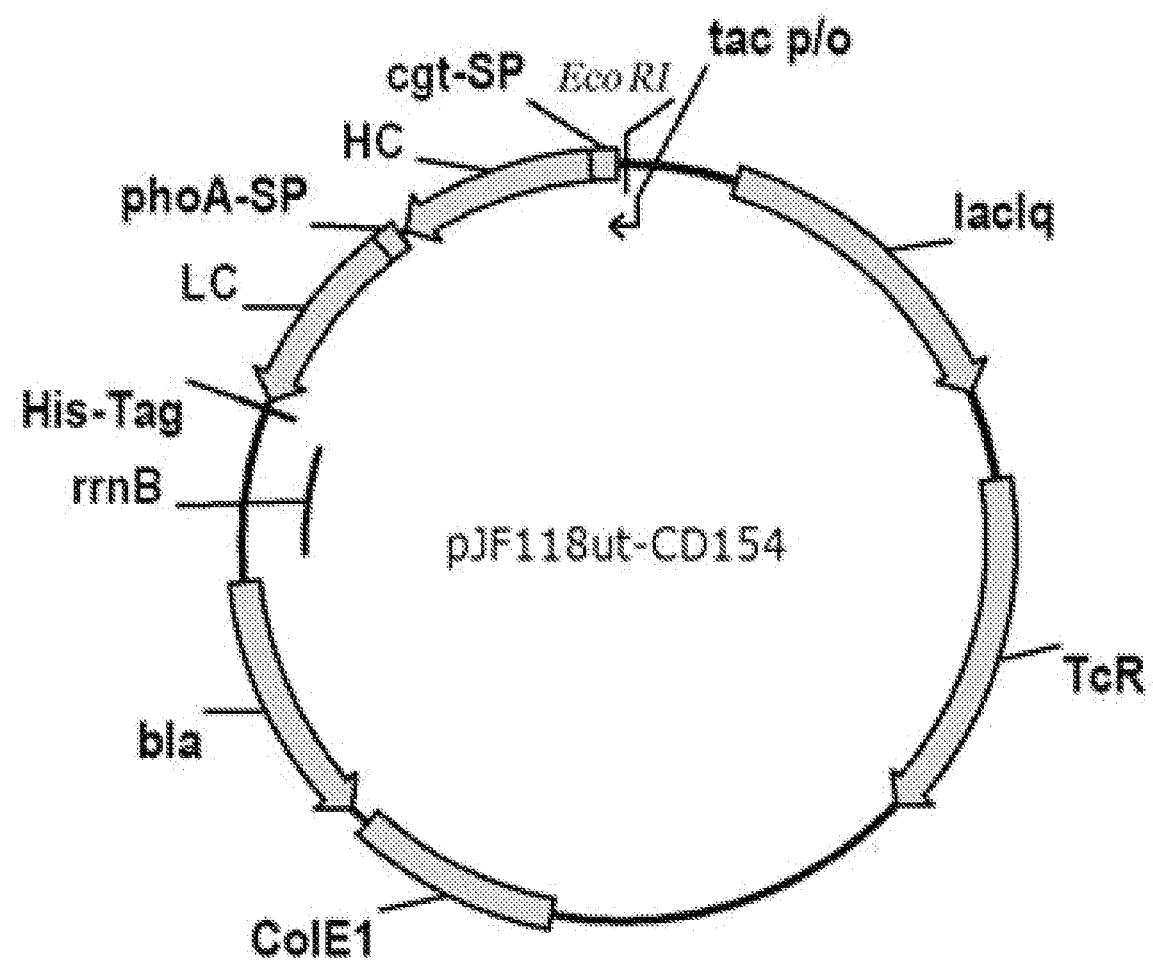
FIG. 2 shows a schematic representation of the expression plasmid pJF118ut-CD154.

The bacterial strain is preferably characterized in that it is Gram-negative bacteria, more preferably a bacterial strain from the family of the Enterobacteriaceae, most preferably a strain of the species *Escherichia coli*.

Open reading frame (ORF) refers to that region of the DNA or RNA that is between a start codon and a stop codon and encodes the amino acid sequence of a protein. The ORF is also referred to as a coding region.

ORFs are surrounded by noncoding regions. Gene therefore refers to the DNA segment which contains all the basic information for producing a biologically active RNA. A gene thus contains not only the DNA segment from which a single-stranded RNA copy is produced by transcription, but also additional DNA segments which are involved in the regulation of this copying process.

Since a gene contains at least one ORF, a gene also encodes at least one protein.

In the ORFs, a base triplet of the DNA encodes, in each case, a certain amino acid or a stop signal. The amino acids encoded as building blocks for the formation of proteins are also referred to as proteinogenic amino acids.

The term "a/the recombinant protein" used in the singular in the context of this invention can also mean multiple different recombinant proteins. Preferably 1 to 3 different recombinant proteins, more preferably 1 recombinant protein or 2 different recombinant proteins, are concerned. The recombinant protein is also referred to as target protein.

The DNA sequence of the lpp wild-type gene of *E. coli* (SEQ ID No. 1, published under EcoGene accession No. EG10544) encodes an unprocessed Lpp protein (Lpp preprotein) which consists of 78 amino acids (SEQ ID No. 2). Here, the first 60 nucleotides encode the signal peptide which controls the secretion of the protein into the periplasm and which is cleaved off after translocation (processing). Respectively situated at the N-terminus and the C-terminus of the processed Lpp wild-type protein are a cysteine residue (Cys) and a lysine residue (Lys) (see FIG. 1B), which are both modified post-translationally by the cell in order to thus ensure the full function of the Lpp protein—namely the connection of the outer membrane to the peptidoglycan layer (also called bacterial cell wall) (Giam et al. 1984, J. Biol. Chem. 259, pages 5601-5605). The terms Lpp, Lpp protein, wild-type Lpp protein and Lpp wild-type protein are used synonymously in the present invention and also referred to as lipoprotein, murein lipoprotein or Braun's lipoprotein in the technical literature. The protein Lpp is encoded by the gene lpp (lpp gene, wild-type lpp gene, lpp wild-type gene).

The bacterial strain according to the invention contains an ORF consisting of the DNA fragment encoding an N-terminal signal peptide, lpp(N) and lpp(C). The protein encoded by said ORF is a Lpp fusion protein. In the context of the present invention, a Lpp fusion protein is to be understood to mean a fusion protein which is composed of two Lpp proteins (called Lpp portions hereinafter, each portion corresponding to a possibly mutated Lpp wild-type protein) and which bears, in the unprocessed form, a signal peptide (SP). FIG. 1A schematically represents such a fusion protein in the unprocessed form. In this case, the N-terminal portion (Lpp(N)), which is linked to the signal peptide in the unprocessed form of the fusion protein, is connected to a C-terminal portion (Lpp(C)). Lpp(N) and Lpp(C) can be connected directly or via an amino acid linker sequence (L) consisting of one to more than one amino acid.

The amino acid sequence of each of the two Lpp portions of the fusion protein can, in each case, either correspond to the processed Lpp wild-type sequence or else comprise, in comparison with the processed Lpp wild-type sequence, up to ten mutations in the amino acid sequence, it not being necessary for the mutations in the two Lpp portions to be identical. In the present invention, the Lpp fusion protein is also called 2xLpp protein and encoded by the 2xlpp gene.

The mutations potentially present in the amino acid sequence of the Lpp fusion protein include substitutions (exchange of amino acids), deletions (absence of amino acids) and insertions (insertion of additional amino acids).

In strains according to the invention, the 2xlpp gene encoding the Lpp fusion protein is present either on the chromosome or on a plasmid. Preferably, the gene encoding the Lpp fusion protein is located on the chromosome.

Preferably, the bacterial strain is characterized in that it does not contain a further gene which encodes a protein having an identity of at least 80% in comparison with the processed wild-type Lpp protein. The sequence of the processed wild-type Lpp protein is specified in SEQ ID No. 2 from amino acid 21 to amino acid 78.

More preferably, the bacterial strain according to the invention does not contain a wild-type lpp gene. Preference is thus given to bacterial strains in which the Lpp fusion protein is the sole Lpp form which occurs in said strains. In this embodiment, the bacterial strains do not form a Lpp wild-type protein and, apart from the Lpp fusion protein, do not form a Lpp variant derived from the Lpp wild-type protein by amino acid exchanges.

Preferably, Lpp(N) and Lpp(C) are connected via a linker consisting of one or more than one amino acids, more preferably one to 20 and especially one to 10 amino acids. What are possible in principle for the linker sequence are all twenty proteinogenic amino acids in any desired order. Preferred amino acids of which the linker sequence is made up are glycine, serine and alanine. In a particularly preferred embodiment, the linker sequence consists of three glycine residues.

It is preferred that the bacterial strain is characterized in that the amino acid sequences encoded by lpp(N) and lpp(C) differ from the amino acid sequence of the wild-type Lpp protein in that
  i) Lpp(N) the C-terminal amino acid lysine present in the wild-type Lpp protein is mutated or
  ii) Lpp(C) the N-terminal amino acid cysteine present in the wild-type Lpp protein is mutated.

In a particularly preferred embodiment, there is mutation of the C-terminal lysine residue in the case of Lpp(N) and of the N-terminal cysteine residue in the case of Lpp(C) in contrast to the Lpp wild-type protein. Most preferably, said residues are deleted (see FIG. 1C). This mutation is intended to prevent the post-translational modifications which normally occur at said amino acid residues.

SEQ ID No. 3 (schematically represented in FIG. 1C) specifies an example of a particularly preferred sequence of a still unprocessed Lpp fusion protein which contains a signal peptide (amino acid 1-20), Lpp(N)ΔLys$_{78}$ (amino acid 21-77) and Lpp(C)ΔCys$_{21}$ (amino acid 81-137), wherein Lpp(N)ΔLys$_{78}$ and Lpp(C)ΔCys$_{21}$ respectively differ from the Lpp wild-type sequence only by the deletion of the C-terminal lysine residue and only by the deletion of the N-terminal cysteine residue and are connected to one another via a linker sequence consisting of three glycine residues. Said protein is designated 2xLppΔin the context of this invention. The 2xLppΔprotein is encoded by the DNA fragment specified in SEQ ID No. 16. Said DNA fragment is designated 2xlppΔ.

Preferably, the bacterial strain is characterized in that, in at least one of the amino acid sequences encoded by lpp(N) or lpp(C), what is present instead of arginine at amino acid position 77 is any other proteinogenic amino acid (numbering and sequence of the amino acids based on the unprocessed wild-type Lpp protein). Particular preference is given to an exchange of the arginine residue at position 77 in at least one of the two Lpp portions for a cysteine residue (R77C exchange).

All signal peptides of lipoproteins from *E. coli* are possible in principle as signal peptide for the translocation of the Lpp fusion protein into the periplasm. Examples are signal peptides of the lipoproteins Lpp, Pal, NlpI, NlpB and OsmB (Hayashi and Wu 1990, J. Bioenerg. Biomembr. 22, pages 451-471). In the context of the invention, the signal peptides can comprise the respective wild-type sequence or a sequence derived therefrom by one or more mutations. The signal peptide of the Lpp fusion protein preferably comprises the sequence of the signal peptide of the wild-type Lpp protein, with differences in the amino acid sequence being present at most eight positions in comparison with the signal peptide of the wild-type Lpp protein.

Preferably, the bacterial strain is characterized in that the N-terminal signal peptide is an amino acid sequence having an identity of at least 80% in relation to the signal peptide of the wild-type Lpp protein. More preferably, the amino acid sequence of the signal peptide of the Lpp fusion protein is identical to the amino acid sequence of the signal peptide of the wild-type Lpp protein, and especially the nucleotide sequence is also identical. The amino acid sequence of the signal peptide of the wild-type Lpp protein is specified in SEQ ID No. 2 from amino acid 1 to 20, and the nucleotide sequence is specified in SEQ ID No. 1 from nucleotide 1 to 60. Preferably, the bacterial strain is characterized in that the N-terminal signal peptide contains, instead of glycine, some other proteinogenic amino acid at amino acid position 14 and is identical to the signal peptide of the wild-type Lpp protein at all other amino acid positions.

More preferably, the bacterial strain is characterized in that the proteinogenic amino acid at position 14 of the N-terminal signal peptide is aspartic acid. In this case, an aspartic acid residue is present at position 14 instead of the glycine residue (G14D exchange) and all other amino acid positions are identical to the signal peptide of the wild-type Lpp protein.

The expression of the 2xlpp gene can be controlled by any promoter which is functional in *E. coli*. In this case, preference is given to promoters which are constitutively active under most growth conditions (e.g., $\sigma^{70}$-dependent promoters), such as, for example, the promoters of the genes gapA, rpiA, mppA, lpp, catB, tufB and proC, and also natural or artificial promoters without a regulatorily active operator region such as, for example, the tetA promoter, the lac promoter, the tac promoter and the trp promoter. The promoter can either comprise the natural sequence or be modulated in terms of its strength by base exchanges.

In a preferred embodiment, the bacterial strain is characterized in that the open reading frame encoding the 2xLpp protein is located in the chromosome instead of the open reading frame encoding the wild-type Lpp protein. In these strains in which the chromosomal lpp wild-type ORF has been replaced with the ORF for the Lpp fusion protein, the expression of the Lpp fusion protein is under the control of the natural lpp promoter. This means that the 2xlpp gene is under the control of the promoter which is also responsible for the expression of the wild-type Lpp protein.

Methods for generating a gene for a Lpp fusion protein according to the invention are known to a person skilled in the art.

Such a gene is generally first generated in vitro and then introduced into the cell. The gene for the Lpp fusion protein can, for example, be produced with the aid of the "overlap extension" PCR method by splicing two DNA molecules which each encode one of the two Lpp portions of the fusion protein (Horton et al. 2013, BioTechniques 54, pages 129-133), with the DNA of the lpp wild-type gene initially serving as template. Alternatively, the 2xlpp gene can also be completely generated by means of gene synthesis.

If the gene for the Lpp fusion protein is to be expressed in the cell by a plasmid, the gene must first be cloned into the plasmid. Suitable for this purpose are all known plasmids propagatable in the chosen bacterial strain, such as, for example, derivatives of known expression vectors such as pJF118EH, pKK223-3, pUC18, pBR322, pACYC184, pASK-IBA3 or pET. Methods for the integration of the 2xlpp gene into the plasmid and for the transformation of the plasmid into bacterial cells are known to a person skilled in the art.

Alternatively, the in vitro generated 2xlpp gene can also be integrated into the chromosome of a host cell by means of various standard methods. This integration can occur either at the natural lpp gene locus, the result being that the lpp wild-type gene originally situated there is replaced with the 2xlpp gene, or else at another site of the chromosome.

The integration into the chromosome can, for example, be achieved by means of the method described in Link et al. (1997, J. Bacteriol. 179, pages 6228-6237) via the mechanism of homologous recombination. To this end, the gene encoding the Lpp fusion protein must first be cloned into the plasmid pKO3, which is then introduced into the cell. What is then carried out with these transformants is the procedure described in Link et al., in which the gene encoding the Lpp fusion protein is incorporated into the chromosome.

Alternatively, the DNA fragment which contains the 2xlpp gene can also be directly transformed into the cell according to the method described by Sun et al. (2008, Appl. Environ. Microbiol. 74, pages 4241-4245) and integrated into the chromosome at the desired site. This involves utilizing the principle of counterselection. First of all, what is introduced at the desired gene locus at which the 2xlpp gene is to be integrated into the chromosome of the cell is an expression cassette containing the cat gene, which encodes a chloramphenicol acetyltransferase, and the sacB gene of *Bacillus subtilis*, which encodes levansucrase. The integration of said cassette is possible by the method of Datsenko and Wanner (2000, Proc. Natl. Acad. Sci. USA. 97, pages 6640-6645), it being possible to identify correct integrants by selection for chloramphenicol resistance. Such cells are resistant to chloramphenicol and, owing to the expression of the sacB gene, sensitive to sucrose. Thereafter, these cells are then transformed with a linear DNA fragment, said fragment containing the 2xlpp gene and the flanks of said fragment comprising DNA sequences homologous to the desired gene locus in order to ensure a site-specific integration of the DNA fragment there. Cells in which an exchange of the cat-sacB cassette for the 2xlpp gene has been effected can be identified owing to the restoration of growth ability in the presence of sucrose. The final verification of the correct integration of the 2xlpp gene into the chromosome can be achieved by means of PCR using oligonucleotides specific for the integration site and subsequent sequencing of the PCR product.

Preferably, the recombinant proteins are heterologous proteins. In the context of the present invention, a heterologous protein is to be understood to mean a protein which does not belong to the proteome, i.e., the entire natural set of proteins, of the bacterial strain.

Preferably, the heterologous protein is a eukaryotic protein, more preferably a protein which contains one or more disulfide bonds or which, in its functional form, is present as a dimer or multimer, i.e., that the protein has a quaternary structure and is made up of multiple identical (homologous) or nonidentical (heterologous) subunits.

The most important heterologous protein classes include antibodies and fragments thereof, cytokines, growth factors, protein kinases, protein hormones, lipocalins, anticalins, enzymes, binding proteins and molecular scaffolds and proteins derived therefrom and pharmacologically effective peptides. Examples of said protein classes are, inter alia, heavy-chain antibodies and fragments thereof (e.g., nanobodies), single-chain antibodies, interferons, interleukins, interleukin receptors, interleukin receptor antagonists, G-CSF, GM-CSF, M-CSF, leukemia inhibitors, stem cell growth factors, tumor necrosis factors, growth hormones, insulin-like growth factors, fibroblast growth factors, platelet-derived growth factors, transforming growth factors, hepatocyte growth factors, bone morphogenetic factors, nerve growth factors, brain-derived neurotrophic factors (BDNF), glial cell line-derived neurotrophic factors, angiogenesis inhibitors, tissue plasminogen activators, blood coagulation factors, trypsin inhibitors, elastase inhibitors, complement constituents, hypoxia-induced stress proteins, proto-oncogenic products, transcription factors, virus-constitutive proteins, proinsulin, parathyroid hormone, prourokinase, erythropoietin, thrombopoietin, neurotrophin, protein C, glucocerebrosidase, superoxide dismutase, renin, lysozyme, P450, prochymosin, lipocortin, reptin, serum albumin, streptokinase, tenecteplase, CNTF and cyclodextrin glycosyltransferases.

Examples of proteins derived from molecular scaffolds are, inter alia, evibodies (derived from CTLA-4), affibodies (of protein A of *S. aureus*), avimers (of human A domain family), transbodies (of transferrin), DARPins (of ankyrin repeat protein), adnectin (of fibronectin III), peptide aptamers (of thioredoxin), microbodies (of microprotein), affilins (of ubiquitin), α-crystallin, charybdotoxin, tetranectin, PDZ domain of the RAS-binding protein AF-6, Kunitz-type domain of protein inhibitors.

A particularly preferred class of proteins consisting of multiple protein subunits are antibodies. Particularly preferably, the bacterial strain is therefore characterized in that the heterologous protein is an antibody or a fragment of an antibody. Antibodies are widely used in research, in diagnostics and as therapeutic, and so there is a need for production methods which are particularly efficient and possible on an industrial scale.

Functional Fab antibody fragments and full-length antibodies can, too, be produced extracellularly by means of the method according to the invention. In this connection, preferred full-length antibodies are antibodies of the IgG class and IgM class, especially the IgG class.

When producing functional Fab antibody fragments, the cell must simultaneously synthesize the corresponding fragment of the light chain (LC), which comprises the domains $V_L$ and $C_L$, and of the heavy chain (HC), which comprises the domains $V_H$ and CH1, and then secrete them into the periplasm and finally into the fermentation medium. Outside the cytoplasm, the two chains then assemble to form the functional Fab fragment.

For the secretion of recombinant target proteins from the cytoplasm into the periplasm, it is necessary to link the 5' end of the ORF of the protein to be produced in frame to the 3' end of a signal sequence for protein export. Suitable for this purpose are, in principle, all signal sequences which allow a translocation with the aid of the Sec or the TAT apparatus. Various signal sequences are described in the prior art, for example the signal sequences of the following genes: phoA, ompA, pelB, ompF, ompT, lamB, malE, Staphylococcal protein A, StII and others (Choi and Lee, Appl. Microbiol. Biotechnol. 64 (2004), 625-635).

What is preferred according to the invention for the secretion of recombinant target proteins from the cytoplasm into the periplasm is the signal sequence of the phoA gene or the ompA gene of *E. coli* or the signal sequence for a cyclodextrin glycosyltransferase (CGTase) from *Klebsiella pneumoniae* M5a1, or the sequence derived from this signal sequence that is disclosed in US 2008/076157 A1. Particular preference is given to the signal sequence for a CGTase from *Klebsiella pneumoniae* M5a1, as disclosed in EP 0 448 093 and specified in the present invention with the sequence SEQ ID No. 4, and to the sequence derived therefrom having SEQ ID No. 5, which is also disclosed in US 2008/076157 A1.

The DNA molecule comprising an in-frame fusion composed of a signal sequence and the ORF of the recombinant target protein is produced by methods known to a person skilled in the art. For instance, the gene of the target protein can be first amplified by means of PCR using oligonucleotides as primers and then, using common molecular-biology techniques, linked to the DNA molecule which comprises the sequence of a signal peptide and which was generated analogously to the gene of the target protein, such that an in-frame fusion, i.e., a continuous reading frame comprising the signal sequence and the gene of the target protein, is formed. Alternatively, it is also possible to produce the entire DNA molecule, comprising the two above-mentioned functional segments, by means of gene synthesis. This signal sequence-recombinant gene fusion can then either be introduced into a vector, for example a plasmid, which is then introduced into the host cell by means of transformation, or be directly integrated into the chromosome of the host cell by known methods. Preferably, the signal sequence-recombinant gene fusion is introduced into a plasmid and the host cell is transformed with said plasmid.

For the secretion of a recombinant target protein consisting of multiple different subunits from the cytoplasm into the periplasm, it is necessary to respectively functionally link the genes of all subunits to be produced (target genes) to a signal sequence for protein export. In this connection, the genes of the various subunits can be linked to the same or different signal sequences. Preference is given to linkage to different signal sequences, and particular preference is given to the linkage of one subunit to the signal sequence of the phoA gene or ompA gene of *E. coli* and the linkage of a further subunit to the signal sequence for CGTase from *Klebsiella pneumoniae* M5a1 having the sequence SEQ ID No. 4 or sequences derived therefrom, such as, for example, the sequence SEQ ID No. 5.

The signal sequence-target gene fusions of the individual subunits can then either be introduced into a vector, for example a plasmid, or be directly integrated into the chromosome of the host cell by known methods. In this connection, the signal sequence-target gene fusions of the individual subunits can be cloned on separate plasmids which are, however, compatible with one another, or they can be cloned on one plasmid. The gene fusions can, in this connection, be combined in one operon or they can be expressed in respectively separate cistrons. Preference is given here to combination in one operon. The two gene constructs can equally be integrated into the chromosome of the host cell, combined in one operon or in respectively separate cistrons. Preference is given here as well to combination in one operon.

Preferably, the DNA expression construct (signal sequence-target gene fusion) consisting of a signal sequence and an ORF encoding the recombinant protein to be secreted is provided with expression signals functional in the chosen bacterial strain (promoter, transcription start site, translation start site, ribosome binding site, terminator).

Suitable as promoters for the gene encoding the recombinant target protein are all promoters known to a person skilled in the art, examples being, firstly, inducible promoters such as the lac, tac, trc, lambda PL, ara or tet promoter or sequences derived therefrom. Secondly, it is also possible to achieve a permanent expression by use of a constitutive promoter, such as, for example, the gapA promoter. However, it is also possible to use the promoter normally linked to the gene of the recombinant protein to be produced.

Using methods known to a person skilled in the art (e.g., transformation), this expression construct (promoter-signal sequence-sequence encoding the recombinant protein) is then introduced into cells which form a Lpp fusion protein. The expression construct for production of the recombinant protein is, for example, introduced on a vector, for example a plasmid such as, for instance, a derivative of known expression vectors such as pJF118EH, pKK223-3, pUC18, pBR322, pACYC184, pASK-IBA3 or pET. Suitable as selection markers for plasmids are genes which encode a resistance to, for example, ampicillin, tetracycline, chloramphenicol, kanamycin or other antibiotics.

According to the invention, preference is therefore given to using a bacterial strain in which the ORF encoding the recombinant protein functionally linked to a signal sequence encoding a signal peptide active in the chosen bacterial strain is preferably further provided with expression signals which are functional in the chosen bacterial strain, preferably a promoter, a transcription start site, a translation start site, a ribosome binding site and a terminator.

The invention further provides a method for fermentative production of a recombinant protein, wherein the bacterial strain according to the invention is cultured in a fermentation medium, the fermentation medium is removed from the cells after the fermentation, and the protein is isolated from the fermentation medium.

The culturing (fermentation) of the cells which express a gene for a Lpp fusion protein and which contain a DNA expression construct consisting of a signal sequence and a recombinant gene encoding the protein to be secreted, linked to functional expression signals, is achieved in a bioreactor (fermenter) by customary fermentation methods known to a person skilled in the art.

The fermentation is preferably carried out in a conventional bioreactor, for example, a stirred tank, a bubble column fermenter or an airlift fermenter. Particular preference is given to a stirred tank fermenter.

The fermentation involves culturing the cells of the protein production strain in a liquid medium over a period of 16-150 h with ongoing monitoring and precise control of various parameters, such as, for example, nutrient feed, partial pressure of oxygen, pH and temperature of the culture. The culturing period is preferably 24-72 h.

Possibilities as culture media (fermentation media) are, in principle, all common media known to a person skilled in the art for culturing microorganisms.

In this connection, it is possible to use, as medium for culturing the bacterial cells, complex media or minimal salts media to which a defined proportion of complex components such as, for example, peptone, tryptone, yeast extract, molasses or corn steep liquor is added. What are preferred for the production of pharmaproteins are chemically defined salts media, i.e., media which, in contrast to the complete medium, have a precisely defined substrate composition.

Examples of suitable minimal salts media for culturing bacterial cells such as, preferably, E. coli cells are, inter alia, the M9 minimal medium, modified minimal medium or Riesenberg mineral medium (Kangwa et al., 2015, AMB Expr 5, page 70) and also the medium FM4 described in US 2008/0254511 A1.

In the method according to the invention, a bacterial strain which expresses a gene for the Lpp fusion protein, and also a gene encoding a recombinant protein connected in frame to a signal sequence encoding a signal peptide, grows in a comparatively short fermentation time in relation to a strain containing Lpp wild-type protein to form comparatively high cell densities and, at the same time, secretes the recombinant protein into the salts medium.

The primary carbon source used for the fermentation can, in principle, be all sugars, sugar alcohols or organic acids or salts thereof that are utilizable by the cells. In this connection, preference is given to using glucose, lactose or glycerol. Particular preference is given to glucose and lactose. Also possible is a combined feeding of multiple different carbon sources. In addition, the carbon source can be initially charged in full in the fermentation medium at the start of fermentation, or nothing or only a portion of the carbon source is initially charged at the start and the carbon source is fed over the course of the fermentation. Particularly preferred in this connection is one embodiment in which a portion of the carbon source is initially charged and a portion is fed. Particularly preferably, the carbon source is initially charged in a concentration of 10-30 g/l, and the feeding is started when the concentration has dropped to less than 5 g/l and is configured such that the concentration is held below 5 g/l.

The partial pressure of oxygen ($pO_2$) in the culture is preferably between 10% and 70% saturation. Preference is given to a $pO_2$ between 20% and 60%; more preferably, the $pO_2$ is between 20% and 40% saturation.

The pH of the culture is preferably between pH 6 and pH 8. Preferably, a pH between 6.5 and 7.5 is set; more preferably, the pH of the culture is held between 6.8 and 7.2.

The temperature of the culture is preferably between 15° C. and 45° C. Preference is given to a temperature range between 20° C. and 40° C., greater preference is given to a temperature range between 25° C. and 35° C., and great preference is given to 30° C.

Preferably, the method is characterized in that the recombinant proteins are purified from the fermentation medium after the removal of the fermentation medium. The purification of secreted proteins from the crude product can be done by customary purification methods known to a person skilled in the art, as are known in the prior art. Customarily, the cells are, in a first step, removed from the secreted target protein by means of separation methods such as centrifugation or filtration. The target protein can then be concentrated, for example by ultrafiltration, and is then further purified via standard methods, such as precipitation, chromatography or ultrafiltration. Particular preference is given here to methods such as affinity chromatography, which utilizes the already correctly folded native conformation of the protein.

A particular advantage of a bacterial strain expressing the 2xlpp gene and a recombinant target protein is that the amount of target protein that is present in the culture medium is higher than in the case of bacterial strains disclosed in the prior art.

Example 3 (see Table 1) provides clear evidence of this. When using a bacterial strain expressing 2xlppΔ(JE5512

2xlppΔ/pJF118ut-CD154), the anti-CD154 Fab titer measured in the culture supernatant was, in absolute terms (i.e., normalized to the same volume), almost twice as high as when using the known lpp3 mutant (JE5512 lpp3/pJF118ut-CD154) and was many times the value determined for the wild-type strain JE5512/pJF118ut-CD154.

Example 4 (Table 2), too, confirms that, when using a bacterial strain expressing 2xlppΔ(JE5512 2xlppΔ/pCGT), there was measurement of, in absolute terms, the highest amount of CGTase in the culture supernatant.

Increased yield is to be understood to mean that the yield of recombinant protein which is released into the culture medium is at least 1.1 times, preferably at least 1.5 times and more preferably at least 1.8 times as high as the yield of recombinant protein in the culture medium that can be produced according to the current state of the art using a wild-type bacterial strain containing a gene for the recombinant protein and/or a wild-type bacterial strain containing a gene for the recombinant protein and expressing additionally a protein for destabilization of the bacterial cell envelope.

A further advantage of a bacterial strain expressing the 2xlpp gene and a recombinant target protein is that the predominant portion of the target protein is secreted into the fermentation medium during culturing.

Example 3 (see Table 1) again provides clear evidence of this. Whereas almost 60% of the anti-CD154 Fab titer were measured in the culture supernatant when using a bacterial strain expressing 2xlppΔ(JE5512 2xlppΔ/pJF118ut-CD154), it was only just under 50% when using the known lpp3 mutant (JE5512 lpp3/pJF118ut-CD154) and only just under 7% in the case of the wild-type strain JE5512/pJF118ut-CD154.

In Example 4 as well, it was possible to measure almost 60% of the recombinant target protein (CGTase) in the supernatant of the culture when using a bacterial strain expressing 2xlppΔ(JE5512 2xlppΔ/pCGT).

Secretion of the predominant portion of the recombinant target protein into the culture medium is to be understood to mean that, based on the amount of target protein produced altogether, preferably over 50% by weight and more preferably over 55% by weight are present in the culture medium.

In contrast to the use of "leaky" bacterial strains, the bacterial strains according to the invention have the advantage that they are culturable in a stable manner, i.e., that the optical density of the culture, which is a measure of the number of intact cells, decreases only a little even in a later culturing phase. As a result, the protein production phase is prolonged compared to "leaky" bacterial strains, the product yield is increased, and there is no rise in the viscosity of the culture medium due to DNA released upon cell lysis. What is last mentioned simplifies the subsequent purification and recovery of the target protein, and this in turn has a positive influence on the process costs.

FIG. 1 shows a schematic representation of the unprocessed Lpp fusion protein (A, 2xLpp) in comparison with the unprocessed Lpp wild-type protein (B, Lpp, sequence specified in SEQ ID No. 2) and of the unprocessed Lpp fusion protein used in the examples (C, 2xLppΔ, sequence specified in SEQ ID No. 3).

The abbreviations used in FIG. 1 have the following meaning:
SP, signal peptide
Cys, amino acid cysteine
Lys, amino acid lysine
Gly, amino acid glycine
L, linker sequence potentially present, consisting of 0-20 amino acids
Lpp, amino acid sequence of the Lpp wild-type protein
Lpp(N), N-terminally located copy of the amino acid sequence of Lpp, which, based on the Lpp wild-type sequence, has mutations at most 10 amino acid positions
Lpp(C), C-terminally located copy of the amino acid sequence of Lpp, which, based on the Lpp wild-type sequence, has mutations at most 10 amino acid positions
Lpp(N)ΔLys$_{78}$, N-terminally located copy of the amino acid sequence of Lpp, which, based on the Lpp wild-type sequence, lacks the amino acid lysine at position 78
Lpp(C)ΔCys$_{21}$, C-terminally located copy of the amino acid sequence of Lpp, which, based on the Lpp wild-type sequence, lacks the amino acid cysteine at position 21-, the dash represents the deletion of an amino acid FIG. 2 shows a schematic representation of the expression plasmid pJF118ut-CD154.

The abbreviations used in FIG. 2 have the following meaning:
tac p/o: tac promoter/operator
EcoRI: cutting site of the restriction enzyme EcoRI
cgt-SP: signal peptide of CGTase
HC: ORF of the heavy chain of the Fab fragment CD154
phoA-SP: phoA signal peptide
LC: ORF of the light chain of the Fab fragment CD154
His-Tag: His tag at the C-terminus of the light chain of the Fab fragment
rrnB: terminator
bla: β-lactamase gene (ampicillin resistance)
ColE1: ColE1 origin of replication
TcR: tetracycline resistance gene
lacIq: repressor of the tac promoter

EXAMPLES

The following examples serve to further elucidate the invention without restricting it.

All the molecular-biology and microbiology methods used, such as polymerase chain reaction (PCR), gene synthesis, isolation and purification of DNA, modification of DNA by restriction enzymes, Klenow fragment and ligase, transformation, P1 transduction, etc., were carried out in the manner known to a person skilled in the art, described in the literature or recommended by the respective manufacturers. The oligonucleotides used were purchased from Metabion International AG (Planegg/Germany).

Example 1: Generation of an *E. coli* JE5512 Strain which Forms an Lpp Fusion Protein (2xLppΔProtein) (2xlpp Mutant)

1. Production of the *E. coli* Strain JE5512 Lpp::Cat-sacB pKD46

The starting strain used for the generation of a strain which forms an Lpp fusion protein was the *E. coli* lpp wild-type strain JE5512 (HfrC man pps) (Hirota et al. 1977, Proc. Natl. Acad. Sci. USA 74, pages 1417-1420, strain available from the National Institute of Genetics, Microbial Genetics Laboratory, NBRP *E. coli,* 1111 Yata, Mishima, Shizuoka, 411-8540 JAPAN).

In this strain, the coding region of the chromosomal wild-type lpp gene (nucleotide 1-237 in SEQ ID No. 1) was first replaced with an expression cassette comprising not only the gene for a chloramphenicol acetyltransferase (cat; UniProt No. P62577), but also the gene for the levansucrase from *B. subtilis* (sacB; UniProt No. P05655). For this purpose, what was used as the template for the amplification of said cat-sacB cassette by means of PCR was a derivative of the plasmid pKO3 (Link et al. 1997, J. Bacteriol. 179, pages 6228-6237; for the sequence of pKO3, see http://arep.med.harvard.edu/labgc/pKO3v.html) in which, by cutting with the restriction enzymes SmaI and Bst1107I and religation of the fragment of 4729 base pairs in size, most of the region between the cat gene and the sacB gene had been removed. The resulting plasmid was designated pKO3-Delta-M13. The PCR to amplify the cat-sacB cassette was carried out using pKO3-Delta-M13 as the template and the oligonucleotides lpp-cat-sac-fw (SEQ ID No. 6) and lpp-cat-sac-rev (SEQ ID No. 7). In this case, the first 60 nucleotides of lpp-cat-sac-fw are homologous to the sequence of the open reading frame (ORF) of lpp that is on the 5' side and the first 60 nucleotides of lpp-cat-sac-rev are homologous to the sequence of the lpp ORF that is on the 3' side. The result was a linear DNA fragment which contained the cat-sacB cassette.

The strain JE5512 was transformed with the plasmid pKD46 (*Coli* Genetic Stock Center CGSC #: 7739), and this resulted in the strain JE5512 pKD46. Competent cells of the strain JE5512 pKD46, which had been produced in accordance with the information from Datsenko and Wanner (2000, Proc. Natl. Acad. Sci. USA 97, pages 6640-6645), were transformed with the linear DNA fragment which contained the cat-sacB cassette. The selection for integration of the cat-sacB cassette into the chromosome of JE5512 at the position of the wild-type lpp ORF was carried out on LB agar plates which contained 20 mg/l chloramphenicol. What were obtained in this way were cells in which the wild-type lpp ORF had been completely replaced with the cat-sacB cassette (JE5512 lpp::cat-sacB pKD46). Integration effected at the correct position in the chromosome was confirmed by means of PCR using the oligonucleotides pykF (SEQ ID No. 8) and ynhG2 (SEQ ID No. 9) and chromosomal DNA of the chloramphenicol-resistant cells as template. Cells of the strain JE5512 lpp::cat-sacB pKD46 express, then, the gene cat encoding a chloramphenicol acetyltransferase and the gene sacB encoding a levansucrase instead of the lpp wild-type gene.

2. Production of a DNA Fragment Encoding a 2xLppA Protein

The DNA fragment encoding a 2xLppΔprotein was produced by the method of "overlap extension" PCR (Horton et al. 2013, BioTechniques 54, 129-33). To this end, chromosomal DNA of JE5512 initially served as template. This contains a wild-type lpp gene.

To generate the DNA fragment containing, inter alia, lpp(N)ΔLys$_{78}$, a PCR was carried out using the oligonucleotides lpp-Allel-fw (SEQ ID No. 10) and lpp-2x-rev2 (SEQ ID No. 11) (PCR1). Using the product of PCR1 as template, a second PCR was carried out using the oligonucleotides lpp-Allel-fw (SEQ ID No. 10) and lpp-2x-rev3 (SEQ ID No. 12) (PCR2), the result being that the product of PCR1 was extended on the 3' side by 41 base pairs.

To generate the DNA fragment containing, inter alia, lpp(C)ΔCys$_{21}$, a PCR was carried out using the oligonucleotides lpp-2x-fw2 (SEQ ID No. 13) and lpp-Allel-rev (SEQ ID No. 14) with chromosomal DNA of JE5512 as template (PCR3). Using the product of PCR3 as template, a further PCR was carried out using the oligonucleotides lpp-2x-fw3 (SEQ ID No. 15) and lpp-Allel-rev (SEQ ID No. 14) (PCR4), the result being that the product of PCR3 was extended on the 5' side by 57 base pairs.

Using the products of PCR2 and PCR4 as template, what was lastly carried out was a fifth PCR using the oligonucleotides lpp-Allel-fw (SEQ ID No. 10) and lpp-Allel-rev (SEQ ID No. 14) as primers. The thereby generated DNA fragment of 1005 base pairs in length contained, inter alia, the signal sequence (SP) of the lpp gene in an ORF connected to a DNA fragment containing, in this example, the coding sequence of the Lpp wild-type protein which lacks the codon for the lysine residue at position 78 (designated lpp(N)ΔLys$_{78}$), a linker sequence (L) consisting, in this example, of three consecutive glycine codons and a C-terminal DNA fragment containing, in this example, the coding sequence of the Lpp wild-type protein which lacks the codon for the cysteine residue at position 21 (designated lpp(C)ΔCys$_{21}$) and also, in addition, respectively approx. 300 base pairs of the 5' and 3' region of the lpp gene locus (SEQ ID No. 16, 2xlppΔ). The 2xLppΔprotein formed by said DNA fragment is schematically represented in FIG. 1C.

3. Production of the *E. coli* Strain JE5512 2xlppΔ

In a next step, the cat-sacB cassette was replaced with 2xlppΔ. To this end, the product from PCR5 was transformed into competent cells of the strain JE5512 lpp::cat-sacB pKD46 by the method of Datsenko and Wanner (see above). The selection for integration of 2xlppΔinto the chromosome of JE5512 lpp::cat-sacB pKD46 at the original position of the wild-type lpp gene was carried out on LB agar plates including 7% sucrose. Since only cells without expression of sacB can grow on sucrose-containing medium, it was possible to select for cells in which the cat-sacB cassette had been replaced with 2xlppΔ(JE5512 2xlppΔ). Integration effected at the correct position in the chromosome was confirmed by means of PCR using the oligonucleotides pykF (SEQ ID No. 8) and ynhG2 (SEQ ID No. 9) and chromosomal DNA of the sucrose-resistant cells as template. The sequence of the integrated 2xlppΔ was verified by sequencing of the PCR product. The resulting strain was designated JE5512 2xlppΔ.

Example 2: Generation of an *E. coli* JE5512 Strain which Contains an Lpp3 Allele (Lpp3 Mutant)

For comparative purposes, a lpp mutant containing the known lpp3 allele instead of the chromosomal lpp wild-type gene was generated proceeding from the *E. coli* strain JE5512 (Giam et al. 1984, Eur. J. Biochem. 141, pages 331-379). The lpp3 allele is distinguished by a mutation which leads to the glycine-to-aspartic acid amino acid exchange at position 14 of the Lpp protein and results in a certain "leakiness" of the cells for periplasmic proteins (see US 2008/0254511 A1).

A PCR was carried out on chromosomal DNA of the lpp3 mutant *E. coli* "W3110 lpp3" (see US 2008/0254511 A1, Example 3) using the oligonucleotides lpp-Allel-fw (SEQ ID No. 10) and lpp-Allel-rev (SEQ ID No. 14). The PCR product containing the lpp3 allele was integrated into the chromosome of the strain JE5512 lpp::cat-sacB pKD46, analogously to 2xlppΔ, as described in Example 1. The correct integration of the PCR product into the chromosome was confirmed by means of PCR and sequencing as described above. The resulting strain was designated JE5512 lpp3.

Example 3: Fermentative Production of a Fab Antibody Fragment Using the 2xlpp Mutant on a 3 l Scale

1. Production of the Plasmid pJF118ut-CD154

The present example describes the production of a Fab fragment of the humanized monoclonal anti-CD154 antibody 5c8, the sequence of which is published in Karpusas et al. (2001, Structure 9, pages 321-329), with the aid of the *E. coli* JE5512 2xlppΔstrain in comparison with the wild-type lpp strain and the lpp3 mutant. The plasmid pJF118ut described in US 2008/0254511 A1 was used as the starting vector for the cloning and expression of the genes of the anti-CD154 Fab fragment. pJF118ut is deposited at the DSMZ-German Collection of Microorganisms and Cell Cultures GmbH (Braunschweig) under the number DSM 18596. The two reading frames for the heavy chain (VH-CH1 domains) and for the light chain (VL-CL domains) of the Fab fragment, inclusive of a signal sequence in each case, were cloned into said plasmid. To this end, the following procedure was carried out: The DNA fragment having SEQ ID No. 17 was produced by means of gene synthesis (Eurofins Genomics). It comprised a gene fusion consisting of i a signal sequence derived from SEQ ID No. 5 and
ii the reading frame for the heavy chain of the Fab fragment, and a gene fusion consisting of i the phoA signal sequence of *E. coli* and
ii the reading frame for the light chain of the Fab fragment and
iii a linker consisting of four amino acids at the C-terminus of the light chain and
iv a hexahistidine tag at the C-terminus of the linker.

Said DNA fragment was cut using the restriction enzymes EcoRI and PdmI and ligated with the expression vector pJF118ut, which had been cut using EcoRI and SmaI. The resulting plasmid, in which the expression of the genes for the heavy and light chain of the anti-CD154 Fab fragment is under the control of the tac promoter, was designated pJF118ut-CD154. FIG. 2 shows the plasmid map of the plasmid pJF118ut-CD154.

2. Production of the Anti-CD154 Fab Antibody Fragment

For the production of the anti-CD154 Fab antibody fragment on a fermenter scale, the strains JE5512, JE5512 lpp3 and JE5512 2xlppΔ were transformed with the plasmid pJF118ut-CD154 by means of the $CaCl_2$ method. The selection for plasmid-containing cells was done by means of tetracycline (20 mg/l).

Production was carried out in 3 l stirred tank fermenters. 1.2 l of a mineral salts medium customary for culturing *E. coli*, including 15 g/l glucose and enriched with complex components (1.5 g/l Hy-Express II (Kerry); 1.0 g/l Amisoy (Kerry); 0.5 g/l Hy-Yest (Kerry)), were inoculated approximately to an $OD_{600}=0.01$ with a preliminary culture which had been cultured at 30° C. in a complex medium (30 g/l phytone peptone (BD Biosciences), 5 g/l yeast extract (Oxoid), 5 g/l NaCl) in a shake flask for approx. 6 h. The inoculation represents time point 0 of the fermentation or the start of fermentation. During the fermentation, a temperature of 30° C. was set and the pH was kept constant at a value of 7.0 by metering in $NH_4OH$ or $H_3PO_4$. At the start, the culture was stirred at 400 rpm and sparged with 2 vvm of compressed air sterilized via a sterile filter. The oxygen probe had been calibrated to 100% saturation under these starting conditions before the inoculation. The target value for the $O_2$ saturation during the fermentation was set to 30%.

Once the $O_2$ saturation had fallen below the target value, a regulation cascade was started in order to restore the 02 saturation to the target value. In this connection, the gas supply was first increased continuously to a maximum of 5 vvm and the stirring speed was then increased continuously to a maximum of 1500 rpm. Feeding with glucose was started 10 h after the start of culturing. About 0.5-1 h before the planned induction, the temperature was lowered from 30° C. to 27° C. The induction of expression was achieved by addition of isopropyl R-D-thiogalactopyranoside (IPTG) to 0.1 mM after a culturing period of approx. 21-23 h.

After a culturing period of 64 h, samples were collected, the cells were removed from the culture medium by centrifugation, and the content of the Fab fragment in the culture supernatant was determined with the aid of a sandwich ELISA assay (see below). To ascertain the amount of the target protein in the entire culture broth, i.e., the sum of Fab fragment present intracellularly and extracellularly, the Fab content in the homogenized culture broth was determined. To this end, 150 µl of culture broth were mixed with 850 µl of 100 mM Tris/Cl buffer (pH 7.4) and the cells were disrupted using a FastPrep homogenizer (FastPrep-24™ 5G, MP Biomedicals). After removal of the cell debris by centrifugation, the clear supernatant was used in the sandwich ELISA assay.

The anti-CD154 Fab fragment was quantified via a sandwich ELISA assay known to a person skilled in the art. This involved using an immobilized anti-Fd heavy chain antibody (The Binding Site, product number: PC075) as catcher and a peroxidase-conjugated goat anti-human kappa light chains antibody (Sigma, product number: A7164) as detection antibody. Quantification was achieved by conversion of the chromogenic substrate Dako TMB+(Dako, product number: S1599) by the peroxidase and the associated absorption change at 450 nm. The ELISA was calibrated using the Fab fragment "Human Fab/Kappa" (Bethyl Laboratories, product number: P80-115).

Table 1 lists the yields of the anti-CD154 antibody fragment in the culture supernatant and the entire culture.

TABLE 1

Anti-CD154 titer in culture supernatant and entire culture after 64 h of fermentation

| Strain | Anti-CD154 Fab (g/l) | |
| --- | --- | --- |
|  | Supernatant | Entire culture |
| JE5512/pJF118ut-CD154 | 0.04 | 0.59 |
| JE5512 lpp3/pJF118ut-CD154 | 0.95 | 1.95 |
| JE5512 2xlppΔ/pJF118ut-CD154 | 1.70 | 2.90 |

Example 4: Fermentative Production of a Cyclodextrin Glycosyltransferase Using the 2xlpp Mutant on a 3 l Scale For the production of a cyclodextrin glycosyltransferase (CGTase) on a 3 l scale, the strains JE5512, JE5512 lpp3 and JE5512 2xlppΔ were transformed with the plasmid pCGT by means of the $CaCl_2$ method. The selection for plasmid-containing cells was done by means of tetracycline (20 mg/l).

The production of the plasmid pCGT for the overexpression of the CGTase is described in Example 4 of US 2008/0254511 A1, and the plasmid map is specified in FIG. 4 of US 2008/0254511 A1. Essentially, the plasmid contains not only the gene for resistance to tetracycline, but also, inter alia, the structural gene of the CGTase from *Klebsiella pneumoniae* M5a1 including the native CGTase signal sequence. The expression of the CGTase-encoding gene is under the control of the tac promoter.

The culturing for fermentative production of the CGTase using the strains JE5512/pCGT, JE5512 lpp3/pCGT and JE5512 2xlppΔ/pCGT was carried out as described in Example 3.

After a fermentation period of 64 h, samples were collected and the CGTase content in the culture supernatant and the homogenized and clarified culture broth (see Example 3) was then determined on the basis of the amount of cyclodextrin (CD) produced enzymatically from starch by means of a CGTase activity assay.

CGTase Activity Assay

Assay buffer: 5 mM Tris HCl buffer, 5 mM CaCl$_2$×2 H$_2$O, pH 6.5

Substrate solution: 10% starch solution (Merck No. 1.01252) in assay buffer, pH 6.5

Assay mix: 0.2 ml of substrate solution+0.2 ml of appropriately diluted CGTase sample (culture supernatant or homogenized and clarified culture broth)

Reaction temperature: 40° C.

Enzyme Assay:

Preadjusting the temperature of substrate solution and CGTase-containing sample (approx. 5 min at 40° C.)

Preparing the assay mix by rapid mixing (whirl mixer) of substrate solution and CGTase-containing sample, the sample being diluted with assay buffer if necessary so that a value of 0.9-1.5 g/l CD is determined in the subsequent HPLC analysis;

Incubating for 3 min at 40° C.

Stopping the enzyme reaction by addition of 0.6 ml of methanol and rapid mixing (whirl mixer)

Cooling the mix on ice (approx. 5 min)

Centrifuging (5 min, 12 000 rpm) and pipetting off the clear supernatant

Analyzing the amount of CD produced by means of HPLC: The analysis was carried out on an Agilent HP 1100 HPLC system with a Nucleodur 100-3 NH2-RP column (150 mm×4.6 mm, Macherey-Nagel) and 64% acetonitrile in water (v/v) as mobile phase, at a flow rate of 2.1 ml/min. Detection was achieved via an RI detector (1260 Infinity RI, Agilent) and quantification was performed on the basis of the peak area and an α-CD standard (Cavamax W6-8 Pharma, Wacker).

Calculation of enzyme activity:
$$A = G*V1*V2/(t*MG) \text{ [U/ml]}$$

A=activity,

G=CD content in mg/l

V1=dilution factor in the assay mix

V2=dilution factor of the CGT-containing sample before use in the assay; if undiluted then: V2=1 t=reaction time in min

MG=molecular weight in g/mol (MG$_{CD}$=973 g/mol)

1 unit (U)≙1 μmol/1 product (CD)/min

Table 2 shows the respectively achieved CGTase yields.

TABLE 2

| Strain | CGTase yield in the culture supernatant after 64 h of fermentation CGTase (U/ml) |
|---|---|
| JE5512/pCGT | 28 10 |
| JE5512 lpp3/pCGT | 540 |
| JE5512 2xlppΔ/pCGT | 619 |

In comparison with the total protein, the proportion of the CGTase released into the medium by JE5512 2xlppΔ/pCGT was—similarly to the anti-CD154 Fab—approx. 58%.

Examples 3 and 4 describe the fermentative production of a medically relevant Fab antibody fragment and of an industrial enzyme, respectively, using various *E. coli* strains. In both cases, the 2xlppΔmutant according to the invention shows superiority in comparison with an lpp wild-type strain and an lpp3 mutant having a "leaky phenotype" with regard to the amount of target protein that is released into the culture medium.

The invention claimed is:

1. A bacterial strain of the species *Escherichia coli* comprising at least one gene encoding a recombinant protein, the bacterial strain containing an open reading frame consisting of i) a DNA fragment encoding an N-terminal signal peptide which mediates the translocation of the protein into the periplasm, wherein the N-terminal signal peptide is an amino acid sequence having the SEQ ID No. 2 from amino acids 1 to 20 or is a signal peptide of the lipoproteins Pal, Nlpl, NlpB or OsmB of *Escherichia coli*, linked to ii) a following DNA sequence (lpp(N)) encoding a lipoprotein (Lpp(N)) as specified in SEQ ID No. 2 from amino acid 21 to 78, or that differs from the amino acid sequence of the wild-type *E. coli* Lpp protein in that the C-terminal amino acid lysine present in the wild-type *E. coli* Lpp protein is mutated, and iii) a further DNA sequence (lpp(C)) encoding a lipoprotein (Lpp(C)) as specified in SEQ ID No. 2 from amino acid 21 to 78, or that differs from the amino acid sequence of the wild-type *E. coli* Lpp protein in that the N-terminal amino acid cysteine present in the wild-type *E. coli* LPP protein is mutated, wherein Lpp(N) and Lpp(C) are connected directly or by a linker consisting of one or more amino acids.

2. The bacterial strain of claim 1, that does not contain a further gene which encodes a protein having an identity of at least 80% in comparison with SEQ ID No. 2 from amino acid 21 to 78.

3. The bacterial strain of claim 1, wherein Lpp(N) and Lpp(C) are connected via a linker consisting of one or more amino acids.

4. The bacterial strain of claim 3, wherein the proteinogenic amino acid at position 77 in at least one of the amino acid sequences encoded by lpp(N) or lpp(C) is cysteine.

5. The bacterial strain of claim 1, wherein the amino acid sequences encoded by lpp(N) and lpp(C) differ from SEQ ID No. 2 from amino acid 21 to 78 in that
Lpp(N) the C-terminal amino acid lysine present in SEQ ID No. 2 from amino acid 21 to 78 is absent or
Lpp(C) the N-terminal amino acid cysteine present in SEQ ID No. 2 from amino acid 21 to 78 is absent.

6. The bacterial strain of claim 1, wherein at least one of the amino acid sequences encoded by lpp(N) or lpp(C), what is present instead of arginine at amino acid position 77 is any other proteinogenic amino acid, the numbering and sequence of the amino acids based on SEQ ID No. 2.

7. The bacterial strain of claim 1, wherein the amino acids which form the linker are selected from the group consisting of glycine, serine and alanine.

8. The bacterial strain of claim 1, wherein the open reading frame encoding the 2xLpp protein is located in the chromosome instead of the sequence specified in SEQ ID No. 1.

9. The bacterial strain of claim 1, wherein the recombinant protein is a heterologous protein.

10. A method for fermentative production of a recombinant protein, comprising: a bacterial strain of claim 1, in a fermentation medium, removing the fermentation medium from the cells after fermentation, and isolating the protein from the fermentation medium.

11. The method of claim 10, wherein the recombinant proteins are purified from the fermentation medium after the removal of the fermentation medium.

* * * * *